US006238589B1

(12) United States Patent
Cooper et al.

(10) Patent No.: US 6,238,589 B1
(45) Date of Patent: May 29, 2001

(54) METHODS FOR MONITORING COMPONENTS IN THE TIW ETCHING BATH USED IN THE FABRICATION OF C4S

(75) Inventors: Emanuel Israel Cooper, Scarsdale; Madhav Datta, Yorktown Heights, both of NY (US); Thomas Edward Dinan, Jr., San Jose, CA (US); Thomas Safron Kanarsky; Michael Barry Pike, both of Hopewell Junction, NY (US); Ravindra Vaman Shenoy, Santa Clara, CA (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/138,442

(22) Filed: Aug. 21, 1998

(51) Int. Cl.[7] ................................................ G01N 31/16
(52) U.S. Cl. ........................... 216/84; 216/85; 216/93; 436/73; 436/102; 436/119; 436/163
(58) Field of Search .................... 216/84, 85, 93, 216/100; 436/73, 83, 102, 119, 129, 163

(56) References Cited

U.S. PATENT DOCUMENTS

| | | | | |
|---|---|---|---|---|
| 3,837,945 | * | 9/1974 | Chiang | 156/8 |
| 4,042,444 | * | 8/1977 | Snyder | 216/93 |
| 4,095,272 | * | 6/1978 | Janzen | 364/497 |
| 4,132,585 | * | 1/1979 | Oxford | 216/93 |
| 4,233,106 | * | 11/1980 | Goffredo | 216/93 |
| 4,749,552 | * | 6/1988 | Sakisako et al. | 422/75 |
| 4,826,605 | * | 5/1989 | Doble et al. | 216/93 |
| 4,886,590 | * | 12/1989 | Tittle | 204/232 |
| 4,927,492 | * | 5/1990 | Panson | 216/109 |
| 5,462,638 | | 10/1995 | Datta et al. | 156/656.1 |
| 5,640,330 | | 6/1997 | Cooper et al. | 364/496 |
| 5,800,726 | * | 9/1998 | Cotte et al. | 216/108 |
| 6,015,505 | * | 1/2000 | David et al. | 216/108 |

FOREIGN PATENT DOCUMENTS

| | | | | |
|---|---|---|---|---|
| 2828547 | * | 1/1980 | (DE) | |
| 4-333581 | * | 11/1992 | (JP) | 216/84 |
| 6-228776 | * | 8/1994 | (JP) | |
| 1188652 | * | 10/1985 | (SU) | |

OTHER PUBLICATIONS

M. Datta, et al., "Electrochemical Fabrication of Mechanicaly Robust PbSn C4 Interconnections", J. Electrochem. Soc., vol. 142, No. 11, pp. 3779–3785 (Nov. 1995).

NN9512417, "Method to monitor and control boil–over of hydrogen peroxide based solutions" IBM Tech. Discl. Bull. 38 (12) 417–417, Dec. 1995.*

Kozhevnikova, E.S. et al "Determination of free acid in the presence of certain heavy metals by turbidimetric titration" Raiona. Volgograd. Politeck. Inst., Volgograd, No. 2, 172–6, from Reg. Zh., Khim. 1966 (18) Pt. I, Abstr. No. 18G2, 1965.*

Greenhow, E. J. et al "Determination of metal salts in the presence of mineral acids by a combination of turbidimetric and catalytic thermometric titrimetry" Analyst (London) 109 (7) 931–5, 1984.*

* cited by examiner

*Primary Examiner*—Anita Alanko
(74) *Attorney, Agent, or Firm*—Scully, Scott, Murphy & Presser; Robert M. Trepp, Esq.

(57) ABSTRACT

Monitoring techniques have been developed for direct/indirect determination of metal etching bath components and for managing their replenishment. The disclosed methods have been successfully employed to make TiW etching a robust process that provides minimized and controlled undercutting of ball limited metallurgy and mechanical reliable C4s. A metal etching solution is monitored and replenished by measuring the sulfate concentration of a hydrogen peroxide, soluble salt, and soluble EDTA salt etchant. Turbidimetric titration conditions are used to measure and compare opaqueness of liquids by viewing light through them and determining how much light is cut off. Additional sulfate is added to maintain the sulfate concentration. Water and/or fresh etchant is added to compensate for evaporation or drag.

24 Claims, 6 Drawing Sheets

FIG. 1(a) 35 mM EDTA in 5M H2O2 .45M KCl: t=0

FIG. 1(b) 35 mM EDTA in 5M H2O2 + KCl: t=4h

METHODS FOR MONITORING COMPONENTS IN THE TIW ETCHING BATH USED IN THE FABRICATION OF C4S

TECHNICAL FIELD

The present invention relates to various methods for monitoring and replenishing the individual components of a peroxide-based metal etching solution and, more particularly, to various methods for monitoring and replenishing $K_2EDTA$ (dipotassium ethylenediaminetetraacetate), and potassium sulfate, which together with hydrogen peroxide, constitute a chemical etching bath for TiW removal in the fabrication of Controlled Collapse Chip Connections (C4s).

BACKGROUND OF THE INVENTION

C4 (Controlled Collapse Chip Connection) is an advanced microelectronic packaging and chip interconnect technique which is currently used in the semiconductor packaging industry. C4 technology is also known and referred to in the art as Flip Chip and solder bump technology.

The basic premise of C4 is to connect chips to ceramic packages by means of solder balls between two surfaces of the units. These tiny balls of electrically conductive solder bridge the gaps between respective pairs of metal pads of the units being connected. C4 provides a very high density electrical interconnection. Unlike other interconnection techniques, which make connections around the perimeter of a chip, C4 allows one or more surfaces of a chip or package to be packed with pads.

As the number of circuits on a chip increases, so does the number of connections needed. C4, which allows more connections in a smaller space than any other packaging technique, is increasingly important commercially.

One method of forming C4s uses an evaporation process wherein solder metal is evaporated through a metal mask in a vacuum chamber. This method, however, is typically less than 5% efficient; more than 95% of the evaporated metal ends up on the evaporator wall and on the metal mask.

An alternative technique described by Datta et al., J. Electrochem. Soc., 142, 3779 (1995) is the electrochemical fabrication of C4s. In this electrochemical fabrication of C4s, a continuous seed layer is required to provide the electrical path for through-mask electrode deposition of PbSn C4s. The seed layers are deposited on a wafer by vacuum deposition techniques, such as sputtering. A layer of photoresist is then applied and patterned to create vias. The solder is then electroplated. For high-end applications, the solder comprises a lead-tin alloy, with a lead content of about 95–97% (heretofore "97/3 PbSn" or "97/3"). After electroplating, the photoresist is stripped and the seed layer between the C4 pads is removed by etching, such that the remaining seed layer under the C4s acts as the ball limiting metallurgy (BLM) for solder pads.

Etching of seed layers is one of the critical processing steps in the electrochemical fabrication of C4s. The seed layers used in the fabrication of 97/3 PbSn C4s consist of Cu as the solderable layer, phased CrCu as the glue layer, and a TiW alloy typically containing about 10% Ti as the adhesion layer. The seed layers between the C4 pads have to be completely removed in order to eliminate electrical contact between C4s while the remaining seed layers under the C4s act as the ball limiting metallurgy (BLM) for solder pads. The size of the seed layers that remains under the C4s is very critical to obtaining mechanically robust C4s. It is essential to maintain large sized TiW pads under the C4s which can sustain the stresses in the flowed C4s. The seed layer etching consists of two steps: (i) electroetching to remove Cu and phased CrCu with minimum undercut of the layers, and (ii) chemical etching to remove the TiW layer.

U.S. Pat. No. 5,462,638 to Datta, et al. provides a chemical etching process based on hydrogen peroxide to selectively remove TiW in the presence of PbSn, CrCu, Cu and Al. The TiW etching bath disclosed in the '638 patent consists of a mixture of the following components: (a) hydrogen peroxide acting as the etchant; (b) potassium sulfate (or another soluble sulfate salt) acting as a passivating agent that forms protective layers over the PbSn C4s; (c) $K_2EDTA$ (or another soluble EDTA salt yielding a solution pH less than 7) acting as a stabilizer for hydrogen peroxide, a buffer, and a complexant for the etched products.

The bath is operated at about 50° C. An end-point detection method permits one to stop etching at a point that corresponds to complete removal of TiW between C4s, while providing a minimum undercut. Etch rate, undercut, and bath stability are some of the criteria that determine the etching process performance.

Both hydrogen peroxide and EDTA in the TiW etching bath degrade with time, leading to pH changes and degradation of etching performance. Accumulation of etched metallic ions in the bath also leads to degradation of the bath components.

The monitoring of TiW etching bath is complicated by the presence of high concentrations of hydrogen peroxide and of potassium sulfate, as well as by the gradual degradation of EDTA. The presence of peroxide precludes the use of common ion-selective electrodes; the high sulfate concentration complicates ion chromatography and several other techniques; and the decomposition products of EDTA are not known or easily determined. In addition, the analytical techniques have to be easy, fast and inexpensive to implement in a manufacturing environment.

In view of the drawbacks mentioned hereinabove, careful monitoring of the individual bath components of a metal etchant solution of the type mentioned above is essential to develop a robust TiW etching process for C4 fabrication that is capable of providing a tight control of TiW undercutting. Moreover, analytical methods are needed for monitoring the individual components of a metal etchant solution that are easy to implement and provide reliable data regarding the individual components of the metal etchant solution. The data found by these analytical methods can be used to determine when the etchant solution needs to be replenished or discarded.

SUMMARY OF THE INVENTION

One object of the present invention is to provide various analytical methods for monitoring and replenishing the individual components of a peroxide-based metal etchant solution which are reliable and overcome all of the drawbacks mentioned with prior art determination methods.

Another object of the present invention is to provide various analytical methods for monitoring and replenishing the effective concentration of soluble EDTA salt such as $K_2EDTA$ and sulfate ions which together with hydrogen peroxide are present in a TiW etchant bath.

A further object of the present invention is to provide various analytical methods of monitoring and replenishing the individual components of a TiW etchant bath so as to provide an etchant bath which is capable of completely removing the seed layer surrounding the C4s while eliminating the undercutting of the seed layer.

These as well as other objects and advantages are achieved in the present invention by a method whereby the effective concentration of the soluble EDTA salt component of a metal etchant solution is monitored and replenished by determining the buffer capacity and the complexing capacity of the metal etchant solution. The sulfate concentration of the metal etchant solution is monitored and replenished in the present invention by employing a method whereby turbidimetric titration with a barium salt solution is used.

Specifically, the present invention provides a method of monitoring and replenishing the effective concentration of soluble EDTA salt present in a metal etchant solution comprising at least a soluble EDTA salt, hydrogen peroxide and optionally a soluble sulfate salt wherein said method comprises determining the buffer capacity, y, of said metal etchant solution by titrating said metal etchant solution with a basic titrant and calculating the difference between titrant volumes at two predetermined pH values, $pH_1$ and $pH_2$ respectively, wherein pH1 and pH2 are pH values where the metal etchant solution is active. Additional EDTA can be added to the etchant solution when y (buffering capacity) is below a prescribed value to replenish the same. Typically, additional EDTA is added when y is in the range of from 0.6 to 1.0 millimoles of base per 10 ml of etching solution.

In another aspect of the present invention, a method is provided that monitors and replenishes the concentration of soluble EDTA salt present in a metal etchant solution comprising at least a soluble EDTA salt, hydrogen peroxide and optionally a soluble sulfate salt wherein said method comprises determining the complexing capacity of said metal etchant solution by thermometric titration of said etchant solution with a transition metal ion from Group 7–11 of the Periodic Table of Elements, and adding additional EDTA thereto so as to maintain the complexing capacity above a predetermined percentage of its initial value.

In yet a further aspect of the present invention, a method of monitoring and replenishing the concentration of sulfate present in a metal etchant solution comprising at least a soluble EDTA salt, a soluble sulfate salt and hydrogen peroxide is provided. In accordance with this aspect of the present invention, the concentration of sulfate present in the metal etchant solution is monitored and replenished by titrating the metal etchant solution diluted with a barium salt solution under turbidimetric titration conditions; comparing the concentration of sulfate to the initial sulfate concentration of the metal etchant solution; and adding additional sulfate salt to the metal etchant solution to bring the sulfate concentration back to its initial concentration. Alternatively, accurate periodic determination of sulfate—the only component which is not used up to a significant extent—enables one to estimate bath losses due to solution drag-out and to add a corresponding amount of fresh solution, before adding more water and optionally hydrogen peroxide to make up for evaporation and decomposition losses.

DETAILED DESCRIPTION OF THE INVENTION

As stated above, the present invention provides various detection methods which can be used to monitor and replenish the concentration of the individual components of a metal etchant solution during the use of said metal etchant solution so that the concentrations of the components can be maintained essentially near the initial concentration of the individual components. Such methods are highly desirable when metal etchant solutions such as those described in U.S. Pat. No. 5,462,638 to Datta, et al., are employed to remove TiW surrounding C4s. This is because it has been observed that hydrogen peroxide and soluble EDTA salt in the etchant bath normally degrade with time, leading to pH changes and degradation of the etching performance.

The present invention has solved the aforementioned problems by using various detection methods to determine the concentration of soluble EDTA salt and sulfate present in the metal etchant solution at any time during its operation. Thus, if the concentration of either falls below its initial concentration, additional amounts of the appropriate component of the metal etchant solution can be added so as to replenish the same.

As stated above, the determination methods of the present invention employ a metal etchant solution which comprises at least hydrogen peroxide and a soluble EDTA salt. The metal etchant solution may optionally contain a soluble sulfate salt. The metal etchant solution may also contain an additional buffering agent such as an acetate salt and/or an additional complexant like nitrilotris (methylene phosphonic) acid. Such metal etchant solutions are well known to those skilled in the art. An example of such a metal etchant solution is disclosed in U.S. Pat. No. 5,462,638 supra, the contents of which are incorporated herein by reference.

Although the concentration of the individual components that make up the metal etchant solution are not critical to the present invention, the metal etchant solution employed to selectively etch the TiW seed layer surrounding the C4s typically comprises from about 10 to about 20 wt. % hydrogen peroxide, from about 5 to about 50 g/l of a soluble EDTA salt and, when present, from about 100 to about 200 g/l of a soluble sulfate salt.

Again it is emphasized that the present invention is not limited to the ranges recited above. Instead, those ranges are given for illustrative purposes only. For example, it is also possible to use ranges that are wider than those of a typically C4 metal etchant solution. Thus, the present invention may also be used when the metal etchant solution comprises from about 1 to about 30 wt. % hydrogen peroxide, from about 0.5 to 5 wt. % soluble EDTA salt, and, optionally, from about 0.2 to about 40 wt. % soluble sulfate salt. More preferably, the metal etchant solution may comprise from about 10 to 20 wt. % hydrogen peroxide, from about 0.7 to 2 wt. % soluble EDTA salt, and, optionally, from about 10 to 20 wt. % soluble sulfate salt.

The term "EDTA salt" is used herein to denote compounds of EDTA that contain a metal from Group 1 or 2 of the Periodic Table of Elements. This includes metals such as potassium, sodium, magnesium, calcium, barium and like metals. Calcium and barium are used only for sulfate-less solutions. An ammonium salt, or protonated amine salt, can also be used. A highly preferred EDTA salt found in metal etchant solutions is $K_2$EDTA.

The term "sulfate salt" is employed herein to denote sulfate-containing compounds which include a metal from Group I of the Periodic Table of Elements; i.e. sodium, potassium, and the like. An ammonium salt, or protonated amine salt, are also contemplated herein. Of these sulfate salts, it is highly preferred that potassium sulfate be present in the metal etchant solution.

The above provides a generic description of the metal etching solutions that can be subjected to the various determination methods of the present invention; the description that follows focuses in on the individual components needing determination and the methods employed in the present invention to monitor and replenish the same.

I. Discussion Concerning EDTA and Methods Employed in the Present Invention to Monitor and Replenish the Same In the above mentioned metal etching solutions, EDTA acts as a complexant for transition metal ions, thus (a) inhibiting their catalytic effect on peroxide decomposition, and (b) helping to prevent precipitation of metal compounds. In addition, EDTA is the main active buffer in the solution in the important pH range between 3–7 and more preferably 4 . . . 5. Experience shows substantial complexing and buffering activity remaining for days after EDTA addition to the etch solution. However, attempts to monitor EDTA show that EDTA changes its chemical identity within hours.

Figure 1A:
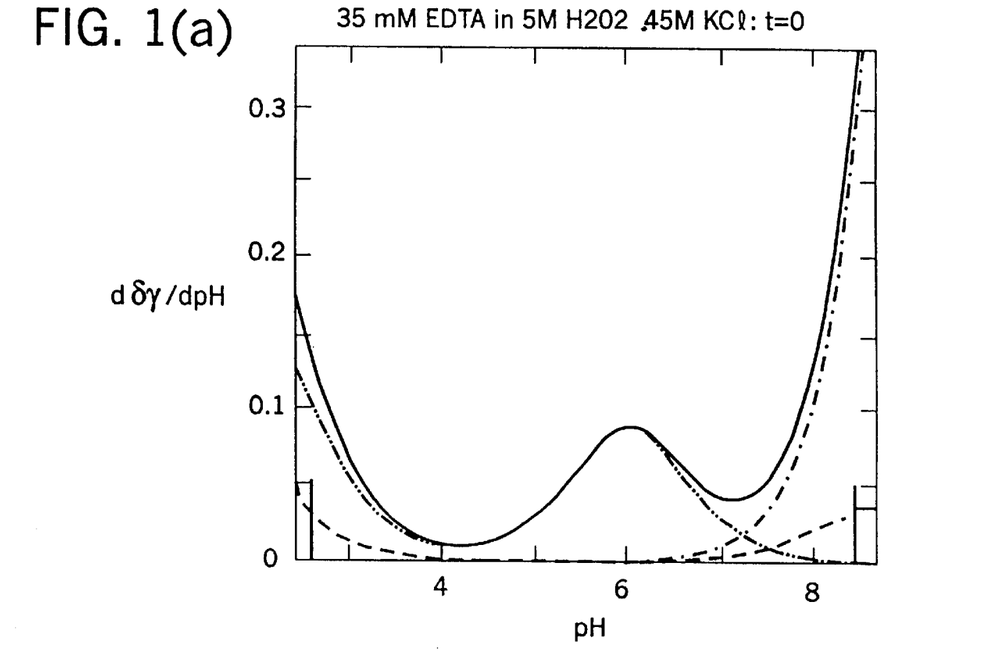
FIGS. 1(a) and (b) show inverted pH titration curves (i.e., titrant volume=f(pH)) for EDTA in a 5 M hydrogen peroxide solution at two different time intervals; (a) immediately after preparation of solution (t=0 hrs.), and (b) after t=4 hrs.
Figure 1B:
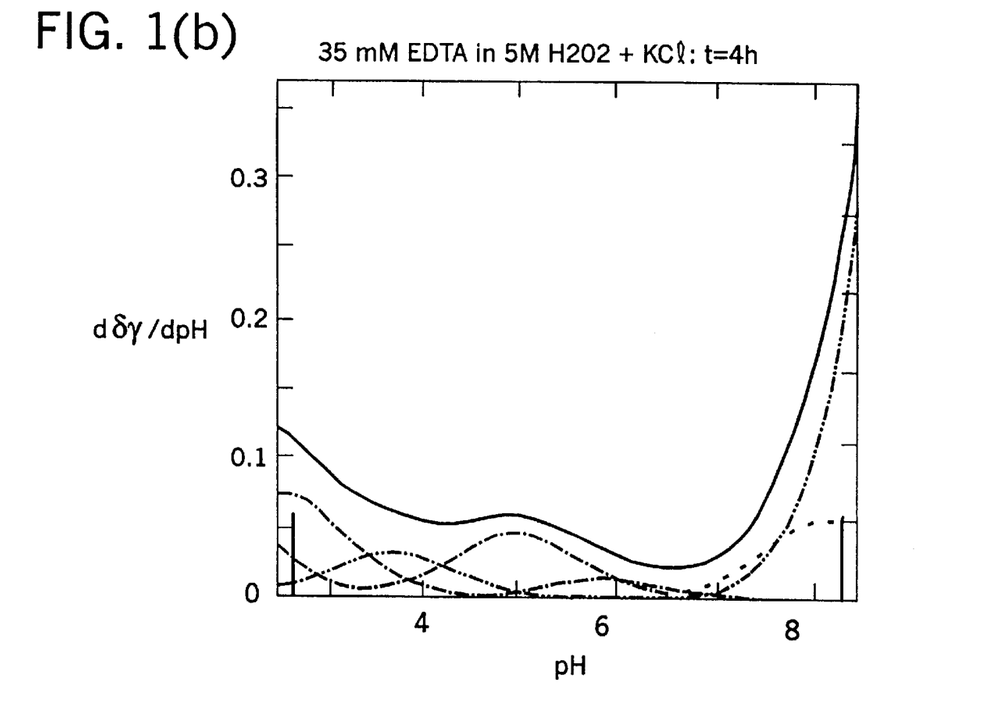

FIGS. 1(a)–(b) show the results of pH titrations performed within minutes of mixing the 50° C. solution, and again after 4 hrs. at the same temperature. (Sulfate was replaced with chloride to add clarity at a pH below 4.) The titration data was analyzed using the pHSPECT program described in U.S. Pat. No. 5,640,330 to E. Cooper and D. Rath, the contents of which are also incorporated herein by reference. The upper continuous curve is the derivative of the titration curve; the lower, broken curves were obtained by its deconvolution and represent the partial contributions of various solution components. The peaks in the displayed curves represent negative logarithms of acidity constants (pKa's), which are characteristic of their compounds. The "t=0" graph shows one major peak at pH 6.1, which coincides with a pKa that belongs to EDTA (the other pKa's of EDTA are out of range). The "t=4hrs." graph shows that EDTA, with its pKa=6.1, is a minor component at t=4hrs., with other compounds (with pKa's around 2.5, 3.7, 5, and 8.2) taking its place. This process continues further. Much of the complexing and buffering activity in the solution, therefore, is due, for most of the bath's life, not to EDTA itself but to its unidentified degradation products. This conclusion, drawn from pH titration results, is also supported by complexometric titrations (not shown).

Since the oxidative degradation of EDTA is clearly a complicated process, the present invention monitors the relevant effects of the buffering/complexing compounds, rather than the compounds themselves. Two separate techniques have been developed, one for buffering capacity, the other for complexing capacity (as expressed by the suppression of metal-ion-catalyzed peroxide decomposition). Bearing in mind the EDTA degradation, it should be understood that in the following, the effective rather than actual concentration of EDTA is determined, i.e. the buffer or complexing capacity of the solution is translated into an equivalent concentration of EDTA salt that would have the same effects, and EDTA salt is replenished as needed accordingly.

The buffering capacity of soluble EDTA salt is determined in the present invention by titrating a metal etchant solution with a basic titrant and calculating the difference between titrant volumes at two predetermined pH values, $pH_1$ and $pH_2$. The choice of $pH_1$ and $pH_2$ may vary depending upon the type of metal etchant solution employed, however, the predetermined pH values should be within a range wherein the metal etchant solution is effective, i.e. the metal etchant solution is still capable of etching material without redepositing oxidized debris on the substrate being etched. This critical range is typically from 3–7 and more preferably 4–5.

Specifically, the pH titration is carried out on a portion of the metal etchant solution that has been first diluted and then the pH of the solution is adjusted to a value lower than $pH_1$ and $pH_2$, preferably between 2 and 3.

In the present invention, $pH_1$ is preferably within the range of $3.5 \leq pH_1 \leq 4.5$; $pH_2$ is preferably $4.5 \leq pH_2 \leq 5.5$; and the value of $pH_2-pH_1$ is preferably 1, although values between 0.1 and 2 can be used, depending on the sensitivity and accuracy of the pH measurement setup.

The dilution of the original metal etchant solution is carried out by adding a sufficient amount of water to the metal etchant solution so as to reduce the original concentration to about 20% or less of its initial value. From about 40 to about 100 ml of water is added per 10 ml metal etchant solution. For data consistency, the amount added should be the same in every test, since the dilution ratio has a slight but measurable effect on pH readings.

The pH of the diluted solution is then determined and adjusted to provide a pH reading below $pH_1$ by adding appropriate amounts of a dilute strong acid such as 0.1–1 M sulfuric acid to the diluted solution. Other dilute acids that can be employed in the present invention include HCl and $HClO_4$.

The pH adjusted sample is then titrated with a dilute volumetric solution of a strong base with a concentration of about 0.1 N, using an automatic titrator or any other titration means that is capable of operating in a constant addition rate mode. As will be obvious to one skilled in the art, the addition rate is selected in accordance to the response time of the pH electrode. In the present invention, an appropriate range with common pH electrodes is 0.5–2 ml/min. Suitable strong bases that can be employed in the pH titration include KOH, NaOH, $(CH_3)_4NOH$.

pH data is obtained on the sample to a pH reading higher than $pH_2$ (e.g. 6 for $pH_2=5$) using a pH meter. The pH data is then analyzed and the titrant volumes at which the pH equals $pH_1$ and $pH_2$ are identified, using interpolation if necessary. Buffer capacity, y, of the solution is then calculated by subtracting the two volumes at pHs of $pH_1$ and $pH_2$. Alternatively, a program that calculates buffer capacity values from titration data can be used, e.g. the PHSPECT program mentioned above.

The present inventors have determined that a buffer capacity, y, in excess of 0.6 and preferably in excess of 0.8 millimole base per 10 ml etching solution, is necessary in an unreplenished bath. When y falls below 0.6 (or 0.8), additional EDTA can be added to maintain y above that value. It is noted that the amount of EDTA to be added varies depending how much below 0.6 the solution is. Typically, in the present invention from about 1 to about 5 g of soluble EDTA salt per liter of solution can be added to replenish the latter.

The complexing capacity of the metal etchant solution is assessed through its capability to absorb an added peroxide-decomposition catalyst without setting off an exothermic decomposition reaction of the $H_2O_2$. Most transition metal ions in Groups 7–11 (IUPAC definition) of the Periodic Table of Elements can serve as titrants for this purpose, Cu(2+) and Fe(3+) being particularly effective in the present invention. The method used in the present invention to measure complexing capacity is thermometric titration, whereby the sample temperature is precisely measured and recorded as a function of the volume of catalyst solution added.

Specifically, the above thermometric titration is carried out by placing a predetermined amount of metal etching solution into a jacketed thermostatted beaker. An insulated beaker can also be employed so long as it is capable of maintaining a near-constant temperature for the duration of the titration. The temperature of the metal etchant solution is kept at a constant temperature within the range of 40°–60° C. The temperature reading of the metal etchant solution within the beaker is measured with either a thermometric titration unit, a thermocouple, thermistor or resistance thermometer which must have a sensitivity of at least 0.01° C. Any of these devices for measuring the temperature can be connected to a suitable recording means.

The titration of the metal etchant solution is then carried out by adding one of the above mentioned transition metal ions in the form of a metal salt solution; e.g. copper sulfate, to the metal etchant solution. Typically, the metal salt titrant is added at a rate of from about 1 to about 3 ml/min to the solution. The temperature of the solution is recorded after every addition or it may be recorded continuously. It is noted that the temperature of the solution decreases upon titrant addition, then stabilizes and then begins to climb steadily. The end point is taken as the end of the steeply descending segment of the temperature curve. At that point, the added transition metal ions are free to catalyze the exothermic peroxide decomposition reaction.

It is noted that in the present invention, additional EDTA can be added so as to keep the complexing capacity above about 10–40% of its initial value. That is, the metal etchant solution should be replenished with EDTA when the complexing capacity decreases to less than about ¼ of its initial value.

II. Potassium Sulfate Monitoring

Monitoring of evaporation or drag-out losses of the etching solution cannot easily be performed by measurements of refractive index, density, or other physical properties, because of the substantial changes in these properties caused by the fluctuations allowed in hydrogen peroxide concentration and (if used) by $K_2$EDTA replenishments. Therefore, it is desirable to determine the sulfate salt accurately in order to get a good estimate of evaporation or drag-out losses, since this component's concentration is the only one which is practically unaffected by chemical reactions. Turbidimetry of sulfate precipitates (usually barium sulfate), in which the turbidity values of sample and standards are compared, is often used for sulfate determination; however, this method is somewhat tedious and not very accurate. A fast, automatic turbidimetric titration with a typical accuracy of about 0.5% and objective end-point was therefore developed. It uses the same traditional chemistry of precipitating the sulfate as barium sulfate and does not require specialized turbidimetry equipment. It also does not suffer from any significant interferences by other solution components.

Specifically, the concentration of sulfate present in the metal etchant solution is determined in the present invention by titrating the etchant solution with a titrant comprising a barium salt solution under turbidimetric titration conditions. By "turbimetric titration conditions" it is meant a titration technique which is capable of measuring and comparing the opaqueness of liquids by viewing light through them and determining how much light is cut off.

In the present invention, the turbidimetric titration is carried out using a fiber-optic probe digital calorimeter that is equipped with a fiber-optic probe and an interference filter. The fiber-optic probe typically has a light path length of from about 0.5 to about 2.0 cm. whereas the interference allows through wavelengths of light in a defined range which is encompassed within the wider range of from about 400 to about 1000 nm. The calorimeter output is sent to a pH/potentiometric port of an automatic potentiometric titrator that can deliver the titrant at a steady rate within the range of from about 0.5 to about 2 ml/min.

The sample is diluted to a sulfate concentration of about $2 \times 10^{-3}$ to about $8 \times 10^{-3}$ M. The diluent is a water-organic solvent mixture containing about 10–50 vol % solvent, preferably 20–40 vol %. Suitable organic solvents that can be employed include: alcohols, esters, ketones and the like, with alcohols being the most highly preferred organic solvent. A preferred alcohol is ethanol, but methanol, tert-butanol, propanol and like alcohols can also be employed.

As mentioned above the titrant is a solution of a soluble barium salt, e.g. $BaCl_2$. Other possible choices include $Ba(NO_3)_2$ and $Ba(ClO_4)_2$. The titrant concentration is about 10–30 times that of the diluted sample, i.e. about 0.02 to about 0.25 M. Preferably the concentration is about 0.1 M. The titrant solution is normally aqueous, although a mixture of water and organic solvent can also be used; in the latter case, the mixed solvent should have the same composition as the mixed solvent in the diluted sample. Using the mixed solvent titrant can improve accuracy under certain conditions (low sulfate concentration, fast titration, high solvent content in the diluted sample), but is not normally necessary for the analysis of the presently discussed etching bath within its normal sulfate concentration range.

The titrant is then added at the steady rate described above and the absorbance at prescribed volumes of titrant is measured and plotted. The end-point on the absorbance plot is easily observed as the sharp intersection of two essentially straight lines. Titration is normally continued for about 1 to 2 ml after the end-point.

The end-point value can be determined by displaying the titration curve's second derivative, in which a sharp peak appears at the end-point. Alternatively, the end-point can be determined graphically as the intersection of two straight segments of the titration curve. If the second-derivative method is used, for best accuracy calibration tests should be run with 2–3 samples of precisely known sulfate concentrations. If the sulfate concentration drops below its initial concentration, additional soluble sulfate salt, hydrogen peroxide and/or water may be added to return the sulfate concentration to its initial value.

To determine the volume of solution lost by drag-out (as distinguished from losses by evaporation and peroxide decomposition), the following procedure can be followed:

1. Measure the initial solution volume $V_0$ and sulfate concentration $C_0$.
2. At $t=t_1$, measure the new solution volume $V_1$ and sulfate concentration $C_1$.
3. The volume of original solution lost by drag-out equals:

$$\frac{C_0 V_0 - C_1 V_1}{C_0}$$

This amount of original solution can now be added to the bath, after which the peroxide concentration can be determined and the volume can be brought back up to $V_0$ by adding a peroxide solution of appropriate concentration.

The following examples are given to illustrate the scope of the present invention. Because these examples are given for illustrative purposes only, the invention embodied therein should not be limited thereto.

EXAMPLE 1

Edta Monitoring

In this example, the effective concentration of EDTA was monitored and controlled by determining the buffer capacity of a TiW etchant bath solution. Specifically, a 10 ml bath sample (aged 24 hours at 50° C.) was diluted with 50 ml water; its pH was then adjusted to about 3 by addition of dilute sulfuric acid. The sample was then titrated with 0.1 M KOH using an automatic titrator in a constant addition rate regime (1.5 ml/min.) and an Orion Ross (trademark) pH electrode. pH data was then recorded to about pH 6. The pH curve was plotted, reviewed, and the titrant volumes at which the pH equals 4 and 5 were identified. The difference between the two volumes, which measures the buffering capacity y as defined in this invention, was calculated to be 0.85 ml.

Figure 2:
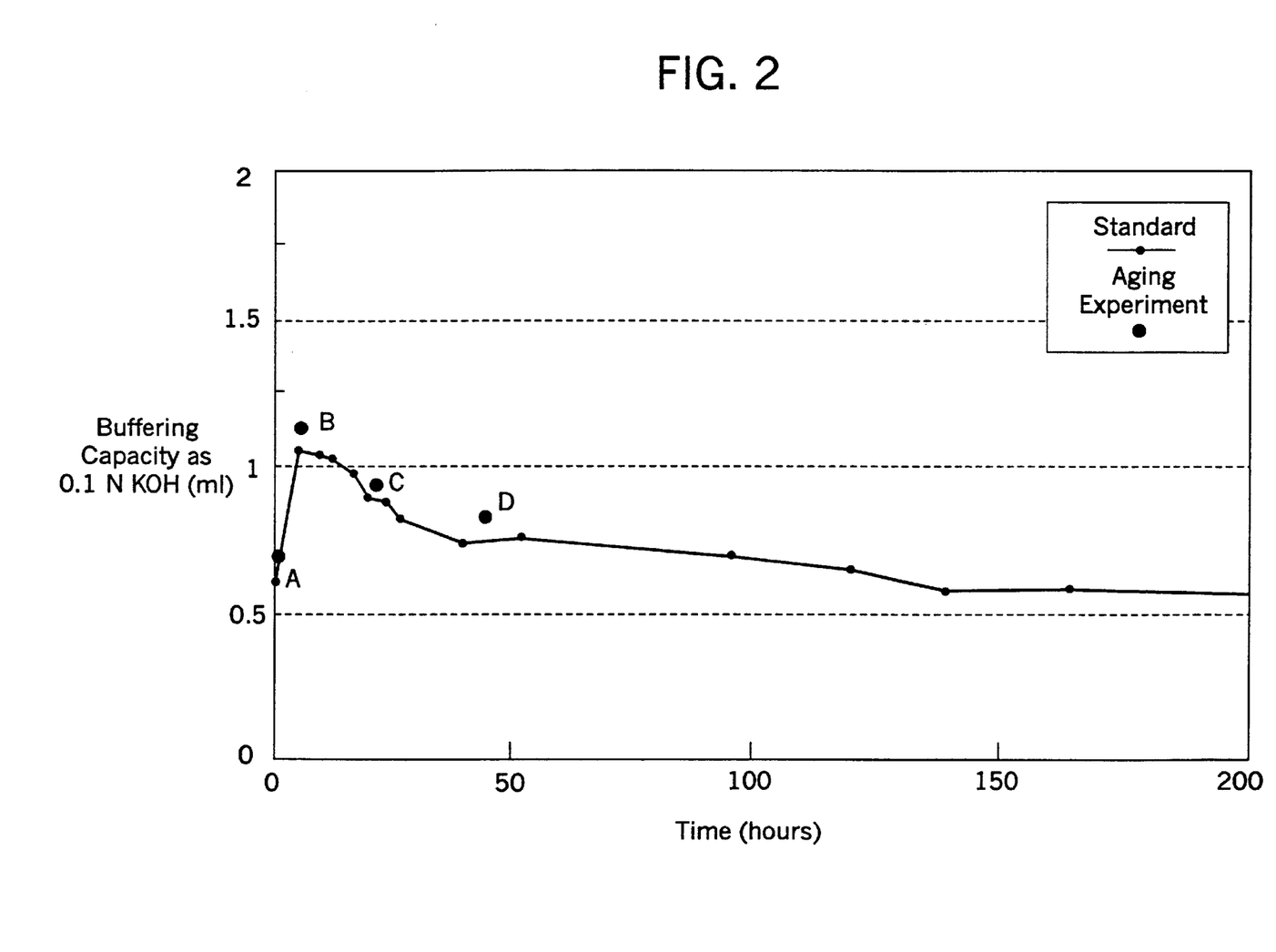
FIG. 2 shows the change in buffering capacity as a function of solution age.

FIG. 2 shows the change in the buffering capacity as the unreplenished solution ages. It was determined that a buffering capacity in excess of 0.8 is necessary; therefore replenishing is necessary in this solution when the buffering capacity dips to $\leq 0.8$.

EXAMPLE 2

Edta Monitoring

In this example, the effective concentration of EDTA was monitored and controlled by determining the complexing capacity of a TiW etchant bath solution using $Cu^{+2}$ titrant.

Figure 3A:
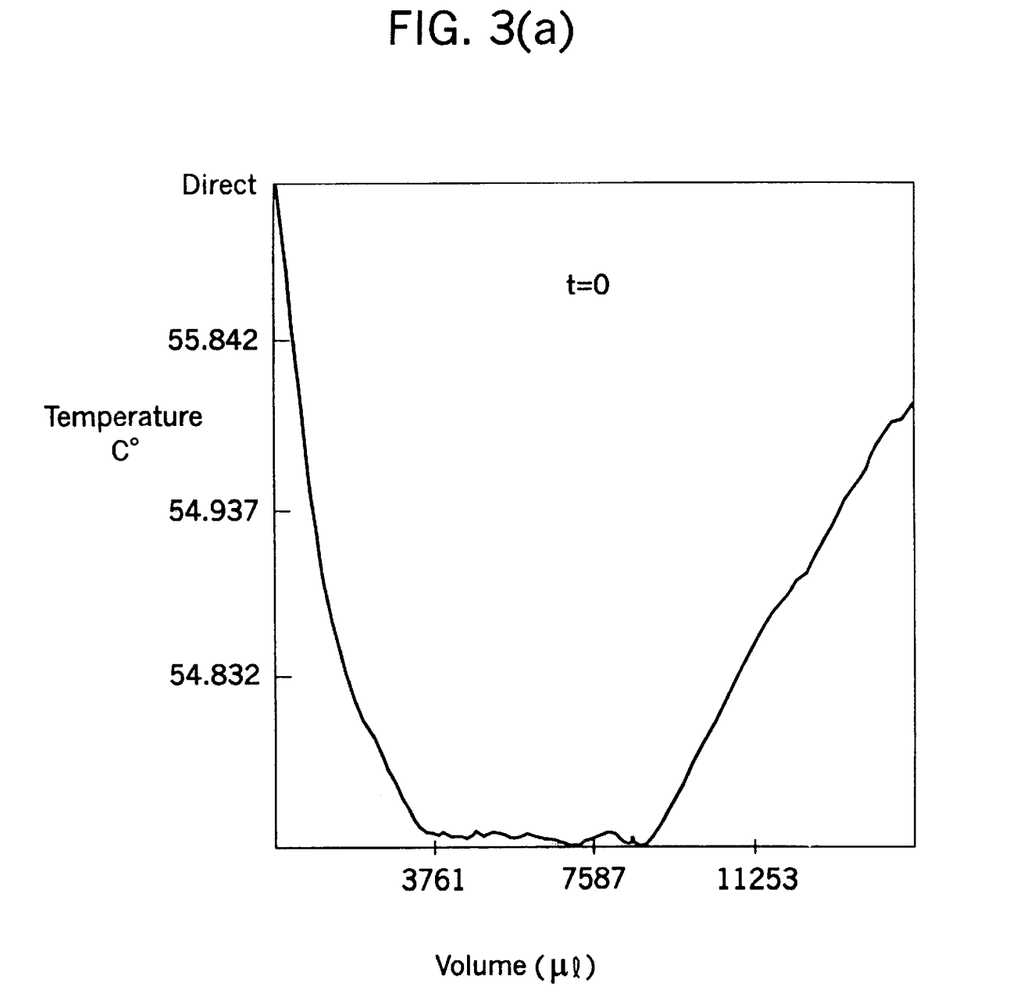
FIGS. 3(a)–(c) show results of thermometric titrations with copper sulfate in (a) a freshly prepared etching solution; and, (b)–(c) after it has been held for various periods of time. The thermometric titration measures the complexing capacity of the solution.
Figure 3B:
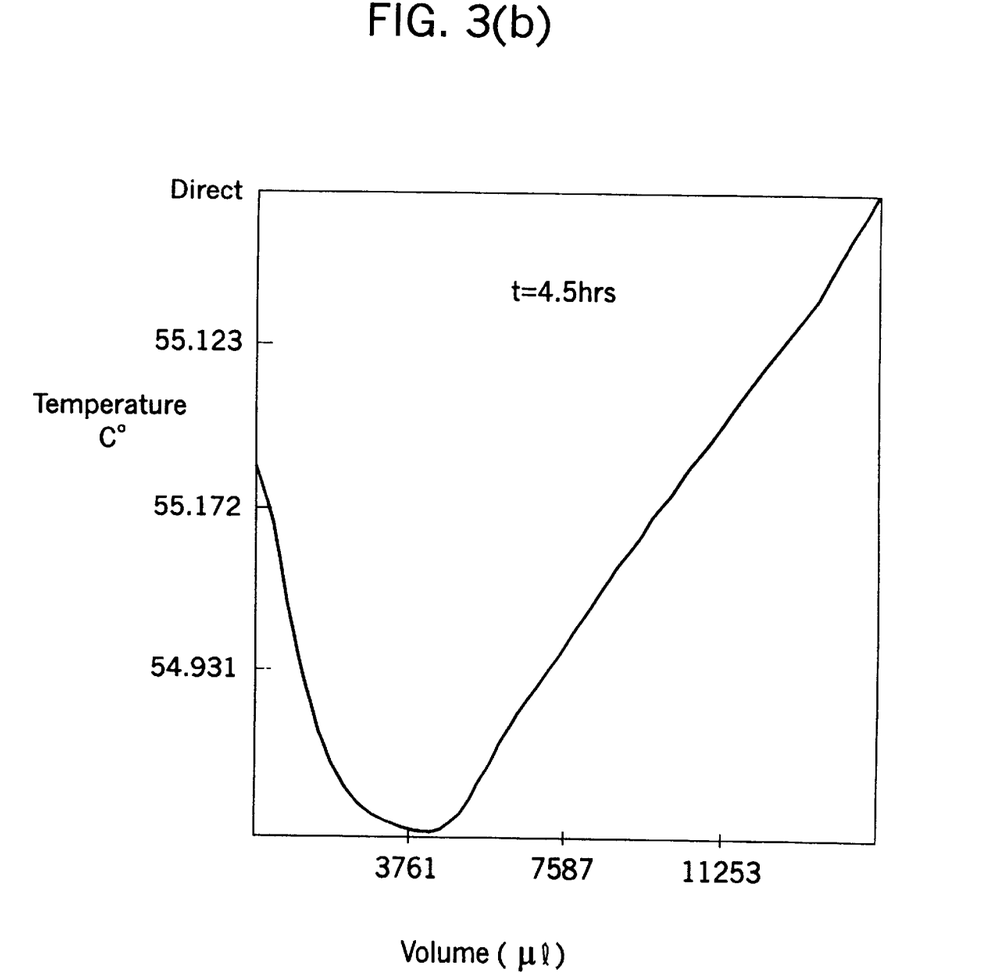
Figure 3C:
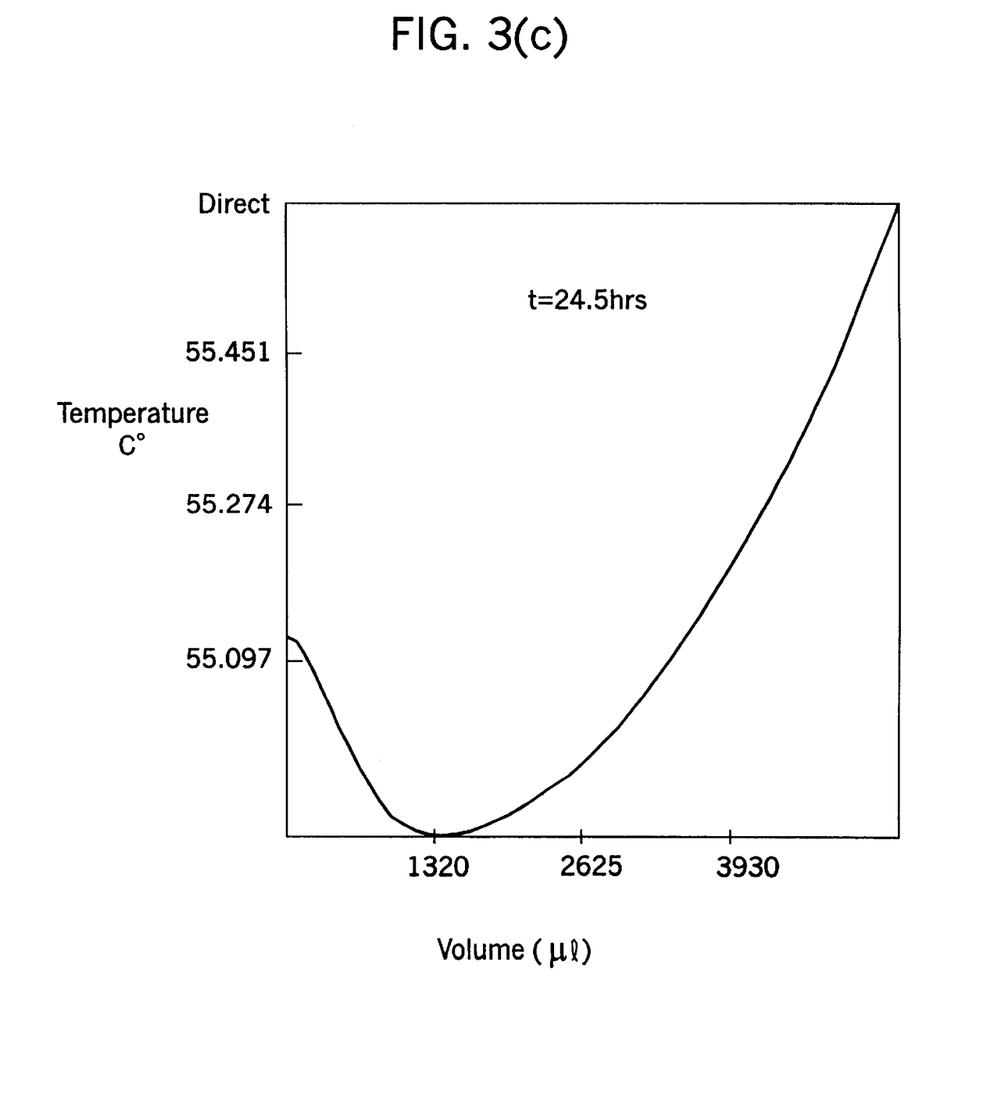

A 50 ml etching solution sample was dispensed into a jacketed thermostatted beaker; its temperature was kept at 50° C. A dedicated thermometric titration unit, made by the Sanda Corp., was used to record temperature and manipulate the data. Just before the start of titration, circulation through the jacket was stopped. The sample was then titrated with a 0.1 M solution of copper sulfate held at room temperature. The temperature of the solution first dropped, then stabilized, then began a steady climb. The end point was taken as the end of the steeply descending segment of the temperature curve; at that point, the added copper ions are free to catalyze the exothermic peroxide decomposition reaction. FIGS. 3(a)–(c) shows examples of thermometric titrations with copper sulfate in a fresh solution and after it had been held at 50° C. for various periods of time.

EXAMPLE 3

Potassium Sulfate Monitoring

A fiber-optic probe digital colorimeter was used (Brinkmann 920); it was equipped with a fiber-optic probe (1 cm light path length) and with a 720 nm interference filter. The colorimeter output (voltage) was sent to the pH/potentiometric port of an automatic potentiometric titrator (a Sanda titrator) that can deliver the titrant at a steady rate.

As a medium for the smooth precipitation of $BaSO_4$, a solution of 25% (v/v) ethanol in water was used. This stock solution was prepared in advance, stirred vigorously for a few minutes and allowed to cool at room temperature, so as to relieve air supersaturation and minimize the occurrence of gas bubbles during titration.

To a 250 ml vessel equipped with a magnetic stirring bar, 180 ml of the 25% (v/v) ethanol solution was added, then 1 ml of the etch-bath solution was precisely measured and added, using an Eppendorf-type pipette. The fiber-optic probe tip was dipped 1–3 cm into the solution; the buret tip was dipped in deeper, and was positioned so that stirring would drive each spurt of liquid almost full circle before reaching the probe. The titrant was a 0.1 M solution of analytical grade barium chloride. Vigorous stirring (enough to generate a small vortex) was started, and the stability of the "absorbance" reading was monitored on the calorimeter display, until noise (usually caused by air bubbles) was at most 0.001 absorbance units. Titrant delivery rate was 24 $\mu$l/sec. The data was collected in absorbance mode.

Figure 4:
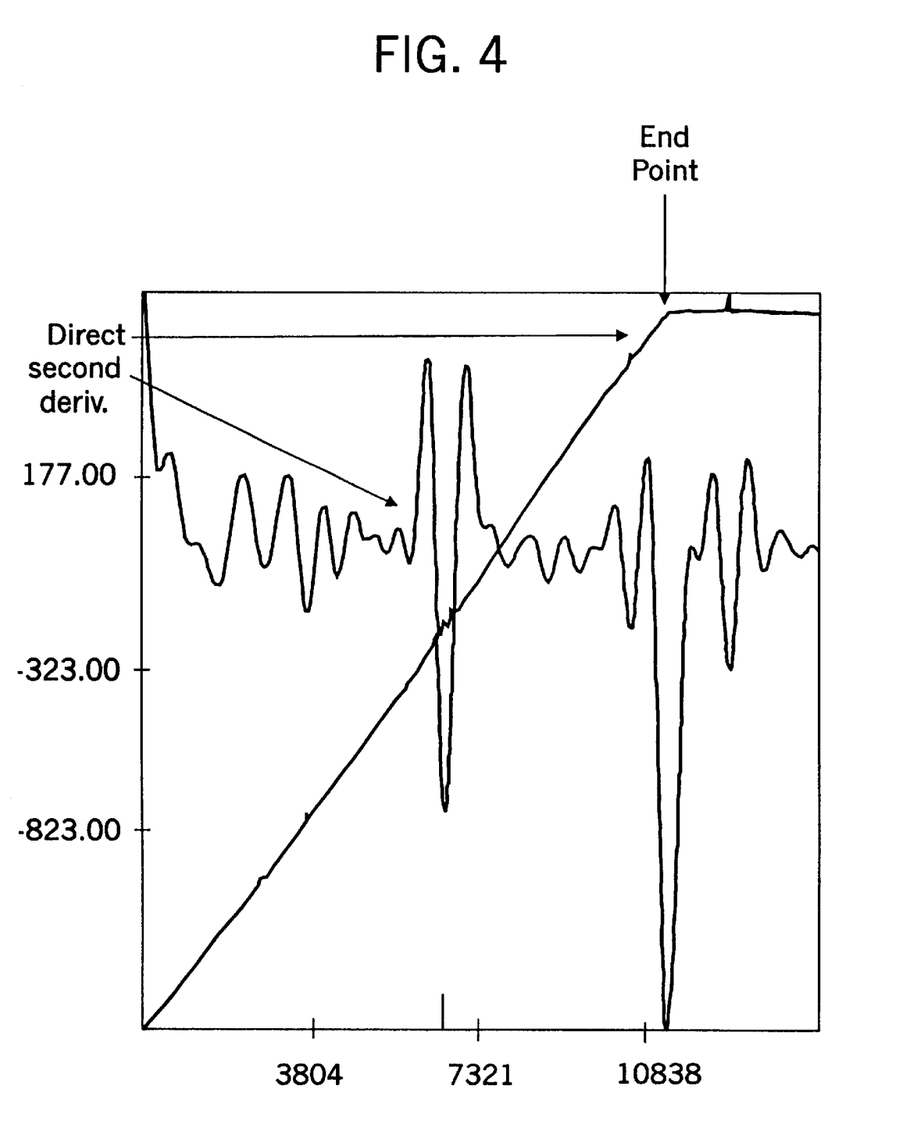
FIG. 4 shows an example of results of turbidimetric titrations with 0.1 M barium chloride. The turbidimetric titration measures the potassium sulfate concentration in the etching solution.

The end-point on the absorbance plot was easily observed as the sharp intersection of two essentially straight lines. Titration was continued for 1–2 ml after the end-point. The end-point value was determined by displaying the titration curve's second derivative, in which a sharp peak appears at the end-point, see FIG. 4. The titration curve and its second derivative are shown.

While this invention has been particularly shown and described with respect to preferred embodiments thereof, it will be understood by those skilled in the art that the foregoing and other changes in form and detail may be made without departing from the spirit and scope of the invention.

Having thus described our invention in detail, what we claim by the Letters Patent is:

1. A method of monitoring and replenishing the effective concentration of soluble EDTA salt present in a metal etchant solution comprising the steps of (a) determining buffer capacity, y, of a metal etchant solution wherein said metal etchant solution comprises at least a soluble EDTA salt and hydrogen peroxide, by titrating said metal etchant solution with a basic titrant and calculating the difference between titrant volumes at two predetermined pH values $pH_1$ and $pH_2$, respectively, so as to obtain y, wherein $pH_1$ and $pH_2$ are pH values wherein said metal etchant solution is still effective; and (b) adding additional EDTA to said solution when said buffer capacity falls below a predetermined value.

2. The method of claim 1 wherein said predetermined value of y is in the range of 0.6 to 1.0 millimoles of base per 10 ml of etching solution.

3. The method of claim 1 wherein said metal etchant solution further comprises a soluble sulfate salt.

4. The method of claim 1 wherein $pH_1$, $pH_2$ and $pH_2-pH_1$ are within the ranges $3.5 \leq pH_1 \leq 4.5$, $4.5 \leq pH_2 \leq 5.5$ and $0.1 \leq (pH_2-pH_1) \leq 2$.

5. The method of claim 1 wherein said metal etchant solution further comprises additional buffers complexant or mixtures thereof.

6. The method of claim 1 wherein said metal etchant solution comprises from about 1 to about 30 wt. % hydrogen peroxide and from about 0.5 to about 5 wt. % soluble EDTA salt.

7. The method of claim 6 wherein said metal etchant solution comprises from about 10 to about 20 wt. % hydrogen peroxide and from about 0.7 to about 2 wt. % soluble EDTA salt.

8. The method of claim 3 wherein said soluble EDTA salt is $K_2EDTA$ and said soluble sulfate salt is potassium sulfate.

9. The method of claim 1 wherein prior to determining y said metal etchant solution is diluted with water and has its pH adjusted with a dilute acid.

10. The method of claim 1 wherein said basic titrant comprises NaOH, KOH or tetramethylammonium hydroxide.

11. A method of monitoring and replenishing an initial concentration of sulfate present in a metal etchant solution comprising titrating said etchant solution diluted with a sample diluent comprising a mixture of water and an organic solvent, with a barium salt solution under turbidimetric titration conditions to obtain a sulfate concentration, wherein said etchant solution comprises at least a soluble EDTA salt, a soluble sulfate salt, and hydrogen peroxide; comparing the sulfate concentration to the initial sulfate concentration present in said etchant solution; and adding additional sulfate to raise said sulfate concentration back to the initial sulfate concentration, or adding water, a fresh etchant solution, or a mixture thereof to compensate for evaporation or drag-out.

12. The method of claim 11 wherein said metal etchant solution further comprises additional buffer, complexant or mixtures thereof.

13. The method of claim 11 wherein said metal etchant solution comprises from about 1 to about 30 wt. % hydrogen peroxide, from about 0.5 to about 5 wt. % soluble EDTA salt and from about 0.2 to about 40 wt. % soluble sulfate salt.

14. The method of claim 13 wherein said metal etchant solution comprises from about 10 to about 20 wt. % hydrogen peroxide, from about 0.7 to about 2 wt. % soluble EDTA salt and from about 10 to about 20 wt. % soluble sulfate salt.

15. The method of claim 11 wherein said soluble EDTA salt is $K_2$EDTA and said soluble sulfate salt is potassium sulfate.

16. The method of claim 11 wherein said turbidimetric titration conditions include the use of a fiber-optic probe digital calorimeter equipped with a fiber optic probe, an interference filter and a pH/potentiometric titration device.

17. The method of claim 11 wherein said organic solvent of sample diluent is an alcohol, an ester, an ether or a ketone.

18. The method of claim 11 wherein said barium salt is barium chloride.

19. The method of claim 17 wherein said organic solvent is an alcohol.

20. The method of claim 19 wherein said alcohol is ethanol.

21. The method of claim 11 wherein said sample diluent comprises from about 50 to about 90 vol. % water and from about 10 to about 50 vol. % organic solvent.

22. The method of claim 21 wherein said sample diluent comprises from about 60 to about 80 vol. % water and from about 20 to about 40 vol. % organic solvent.

23. The method of claim 11 wherein said $BaCl_2$ mixture is added to said metal etchant solution at a rate of from about 0.5 to about 2 $\mu$l/sec.

24. The method of claim 11 wherein the barium salt used as titrant is dissolved in a mixture of water and an organic solvent of about the same composition as the mixture used to dilute the sample.

* * * * *